United States Patent [19]

Burden et al.

[11] 4,075,783
[45] Feb. 28, 1978

[54] BEE ATTRACTING COMPOSITION AND METHOD OF USE

[75] Inventors: Ivor R. Burden, Aptos; George W. Reilly, Clovis, both of Calif.

[73] Assignee: Custom Chemicides, Inc., San Leandro, Calif.

[21] Appl. No.: 698,154

[22] Filed: Jun. 21, 1976

[51] Int. Cl.$^2$ ............................................. A01G 7/00
[52] U.S. Cl. ................................. 47/1.41; 6/12 M; 426/1; 424/84
[58] Field of Search ................... 47/1.41; 426/1, 583; 424/84; 6/12 M

[56] References Cited

U.S. PATENT DOCUMENTS 2,895,829   7/1959   Feo et al. ................................. 426/1

FOREIGN PATENT DOCUMENTS 141,203   11/1946   Australia ............................. 6/12 M
970,209   7/1975   Canada ................................. 426/1
13,160   7/1966   Japan ................................. 424/84

OTHER PUBLICATIONS

American Bee Journal, Jan. 1965, Boch, et al., p. 166.
American Bee Journal, May 1965, p. 167.
American Bee Journal, June 1971, p. 231.

*Primary Examiner*—Robert E. Bagwill
*Attorney, Agent, or Firm*—Flehr, Hohbach, Test, Albritton & Herbert

[57] ABSTRACT

A dry powder of water wettable and dispersable bee attracting composition including whey, sucrose and wetting and dispersing agents. The powder is dispersed in water and sprayed onto a crop area requiring honey bee pollination during the blooming period to attract bees and to maintain them in the crop area for increased pollination. Alternatively, the powder may be dusted onto the crops.

3 Claims, No Drawings

BEE ATTRACTING COMPOSITION AND METHOD OF USE

BACKGROUND OF THE INVENTION

Various compositions have been employed as a feed supplement for bees to increase the population of bee colonies. The formulas are fed to the bees in either a dry form or in a concentrated slurry in the vicinity of the hives. One such formulation is disclosed in an article entitled "Commercial Feeding" by Stanger and Gripp, *American Bee Journal,* Vol. 112:417–4 (November 1972) employing soybean flour, food wheast, and sugar syrup. Wheast is a yeast product derived from by-products in the manufacture of cottage cheese. Another formulation disclosed in the above article includes a minor portion of dry skim milk (2%) together with a major portion of sugar (90%). Further wheast-based feeds for honey bees are disclosed in an article entitled "Supplemental Feed of Honey Bees", by Stanger and Laidlaw, *American Bee Journal,* Vol. 114(4): 138–141 (April 1974). Such formulations comprise a major portion of sugar syrup together with feed wheast.

Another bee feed composition is disclosed in Feo et al U.S. Pat. No. 2,895,829, for maintenance of the strength of a bee colony. For this purpose, a grape pomace is added to the composition which also includes protein, carbohydrates, and fats as a lure or scent to make the food more acceptable to the bees. The composition is specifically stated to be emloyed as a substantially dry mixture.

SUMMARY OF THE INVENTION AND OBJECTS

In accordance with the present invention, the productivity of a crop area requiring honey bee pollination is significantly increased by spraying or dusting a bee attracting composition over the crop area during the blooming period. The preferred bee attractant spray comprises a dilute aqueous dispersion of milk protein, sugar and wetting and dispersing agents for the milk protein. A particularly effective and relatively inexpensive source of milk protein and sugar is whey and sucrose. A convenient way to form the spray composition is to provide the farmer with a dry composition containing the above solids for mixing immediately prior to spraying of the crops. This powder can also be dusted onto the crops.

It is an object of the invention to increase the productivity of a crop area requiring honey bee pollination by spraying or dusting the area with a bee attracting composition.

It is another object of the invention to provide an inexpensive and highly effective spray composition to accomplish the foregoing objective.

It is a further object of the invention to provide a water wettable and dispersable dry powder which can be either dispersed readily in a volume of water at the crop site for spraying or dusted onto the crop site.

Further objects and features of the present invention will be apparent from the following description in which the preferred embodiment is set forth in detail.

Detailed Description of the Preferred Embodiments

It is well known that honey bees are essential in the production of many agricultural crops including fruits and nuts, forage seeds, vegetable seeds, vegetables, and tree seeds. Important crops of this type include almonds, avocado, ladino clover seed, plums, prunes, melons, (honeydew and cantalope), and alfalfa seed. These crops vary in their required number of visitations of the honey bees for pollination. For example, almonds and alfalfa require about three bee visitations to the blooming flower while watermelon requires about 12 visitations. For maximum productivity, it is desirable to maintain a peak bee level in the crop during the blooming period, say on the order of 3 to 10 days.

It has been discovered that the productivity of the crop area requiring honey bee pollination may be significantly increased by spraying or dusting a bee attracting composition over the crop area during the blooming period. In this manner, bees are attracted and maintained in the crop area for sufficient time to accomplish the required numbers of visitations for pollination.

The specification will first describe the spray composition form of the invention. For convenience, it is desirable to form a dry powder of water wettable and dispersable bee attracting composition which may be transported to the crop site and rapidly mixed with a volume of water for spraying as by airplane, or ground power sprayers. A preferred dry powder comprises whey, sugar (sucrose) and wetting and dispersing agents for the whey.

A suitable formulation of the bee attracting composition of the present invention is set forth in the following table:

TABLE I

| Ingredient | Dried Whey % Range | Specific |
|---|---|---|
| Whey | 45 – 85 | 66.5 |
| Powdered Sugar (Sucrose) | 10 – 50 | 30.0 |
| Dispersing Agent (Sodium Lignosulfonate) |  | 2.0 |
| Wetting Agent (75% Active Alkyl Aryl Sulfonate) |  | 1.5 |

The dried whey of the composition is effective for attracting and maintaining the bees. It is believed that the lactose serves as an attractant and feed supplement. It is also believed that the protein serves as a feed supplement. The protein function is substantiated because sugar solutions sprayed on crops are not successful in maintaining the bees in a crop area for sufficient time for increased productivity while the present whey-containing composition does.

Any conventional dried whey product may be employed in the present invention. As defined herein, the term "whey" refers to crude or processed (e.g., partially delactosed) whey powder. One effective source of whey is supplied by Foremost Foods Company under the designation M.N.C (milk nutrients concentrated). This partially delactosed product includes a major portion of lactose and minor portions of proteins and minerals. A typical composition is 52% lactose, 16.7% protein, and 15.8% minerals. The powdered sugar (sucrose) powder of the present invention may be derived from any conventional source such as common table sugar. It serves as a combined nutrient and bee attracter. It is apparent that whey supplies protein and sugar (lactose) to the composition. A suitable composition includes about 10 to 25% by weight protein and about 60 to 75% by weight combined sugar content (lactose and sucrose). The remainder primarily comprises minerals and vitamins.

Minerals and vitamins are present in the whey and so in the final composition. They also serve as desirable feed supplement for the bees to maintain them in the desired area.

A suitable dispersing agent (e.g., sodium lignosulfonate) and wetting agent (e.g., alkyl aryl sulfonate) are provided to wet and disperse the dried whey. Other conventional wetting and dispersing agents may be employed for this purpose.

Some bee feed compositions have included pollen as an ingredient. However, it has been found that the inclusion of pollen in the spray composition of the present invention is not desirable because it attracts pollen worker bees. Such bees remove the bee attractant from the crop area and do not assist in pollination.

The concentration of spray composition per acre of crop varies depending upon the nature of the crop. Typical concentrations may be found in the following table:

TABLE II

| Crop Type | Concentration - Dry Powder (lbs) Per Acre |
| --- | --- |
| Deciduous Nut Crops (almonds, macadamia, pistachio) | 5 - 15 |
| Deciduous Fruit Crops (apples, apricots, cherries, olives, pears, peaches, nectarines, plums, and prunes) | 5 - 15 |
| Alfalfa and ladino seed, vetch, trefoil, red clover | 5 |
| Cotton, cucumbers, squash, melons, pole beans, safflower, cranberries, strawberries | 5 |
| Corn and soybean hybrids | 5 |
| Avocado and citrus | 5 - 15 |
| Vegetable and flower seed crops | 5 |

The concentration of dried powder in water is determined by the type of spray equipment. For example, a suitable concentration for a typical airplane sprayer is on the order of 1 pound of dry powder per gallon of water. On the other hand, a suitable concentration for a conventional full volume ground power sprayer is about 1 pound per 100 gallons of water applied at 500-800 gallons of dilute spray per acre.

The advantages of spraying the present bee attracting and feed supplement composition varies from crop to crop. For example, ladino clover is a very low nectar producing flower and therefore is not very attractive to bees. The present composition increases the attractiveness of the flower to the bees and offers them necessary added nutrients.

The present invention is very beneficial to melons and cucumbers. For these crops, it is important to transfer a sufficient number of pollen grains (e.g., 500 to 1,000) to the female flower to increase the potential for fruit set. This also decreases the potential for misshapen and undersized fruit due to inadequate pollination.

Plums are relatively unattractive to bees as a source of pollen and nectar. The present composition can increase potential pollination and fruit set by attracting and maintaining the bees in an orchard.

Production of prunes and plums requires cross pollination. However, neither prunes nor plums are very attractive to honey bees. The present composition also attracts honey bees and maintains them in the orchard to increase potential pollination and corresponding fruit set.

Side-by-side tests were performed comparing the productivity of (a) a field of unsprayed seed alfalfa with (b) a field of sprayed alfalfa, both in full bloom. The treatment comprised five pounds of the foregoing powder in five gallons of water per acre applied every other swatch by airplane at 2½ pounds of product per acre. The yield at harvest of the untreated crop was 1,000 per acre of seed. In contrast, the yield of crop of the sprayed area comprised 1,450 pounds per acre seed, a major increase in productivity.

The foregoing disclosure refers to the preferred bee attracting composition of the present invention. It should be understood that other bee feed supplement materials may also be employed such as described in the aforementioned Stanger and Gripp article. However, tests have been performed which indicate that the present composition is superior to the latter material including wheast and sugar syrup in terms of crop productivity. Furthermore, wheast is now in short supply whereas the whey product of the present invention is in ready supply and relatively inexpensive.

In an alternative embodiment, the dry powder of the present invention is dusted in dry form onto the crop area. Approximately the same concentration of dry powder may be applied per acre of crop as with the solids content of the foregoing spray composition. In this dry form, wetting and dispersing agents may be eliminated. However, it is preferable to include such agents for further dispersion when the crop is contacted with rain or dew.

The bee attractant of the present invention, in dry or spray form, may be dispersed into the crop area alone or in combination with other materials which are sprayed or dusted onto the crop area, such as a fungicide.

What is claimed is:

1. A method for increasing the productivity of a crop area requiring honey bee pollination, comprising the step of spraying an aqueous bee attracting spray composition over the crop area during the blooming period in sufficient quantity to attract bees and to maintain them in the crop area for pollination, said bee attracting composition comprising a dilute aqueous dispersion of about 10 to 25% by weight milk protein, about 60 to 75% by weight sugar, and wetting and dispersing agents for said milk protein.

2. The method of claim 1 in which said sugar consists essentially of lactose and sucrose.

3. A method of increasing the productivity of a crop area requiring honey bee pollination, comprising the step of spraying an aqueous bee attracting spray composition over the crop area during the blooming period in sufficient quantity to attract bees and to maintain them in the crop area for pollination, said bee attracting composition comprising a dilute aqueous dispersion of 45 to 85% by weight whey, 10 to 50% by weight sucrose, and wetting and dispersing agents.

* * * * *